(12) United States Patent
Devic et al.

(10) Patent No.: US 8,252,964 B2
(45) Date of Patent: Aug. 28, 2012

(54) PROCESS FOR THE PURIFICATION OF 2,3,3,3-TETRAFLUORO-1-PROPENE (HFO-1234YF)

(75) Inventors: Michel Devic, Millery (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/001,663

(22) PCT Filed: Jun. 8, 2009

(86) PCT No.: PCT/FR2009/051074
§ 371 (c)(1),
(2), (4) Date: Dec. 28, 2010

(87) PCT Pub. No.: WO2010/001025
PCT Pub. Date: Jan. 7, 2010

(65) Prior Publication Data
US 2011/0105809 A1    May 5, 2011

(30) Foreign Application Priority Data
Jul. 3, 2008  (FR) ..................................... 08 54514

(51) Int. Cl.
*C07C 17/38* (2006.01)
(52) U.S. Cl. ....................................... 570/177; 570/179
(58) Field of Classification Search .................. 570/177, 570/179
See application file for complete search history.

(56) References Cited

U.S. PATENT DOCUMENTS

| | | | |
|---|---|---|---|
| 5,396,000 A | 3/1995 | Nappa et al. | |
| 7,041,264 B2 | 5/2006 | Horiba et al. | |
| 7,084,315 B2 | 8/2006 | Corr et al. | |
| 7,094,935 B2 | 8/2006 | Suzuki et al. | |
| 2010/0162738 A1* | 7/2010 | Low et al. ........................ | 62/101 |

FOREIGN PATENT DOCUMENTS

| | | |
|---|---|---|
| JP | 1040507 | 2/1989 |
| JP | 2002/226411 | 8/2002 |
| WO | WO 2005/108334 | 11/2005 |
| WO | WO 2007/079431 | 7/2007 |
| WO | WO 2007/144632 | 12/2007 |
| WO | WO 2008/001844 | 1/2008 |
| WO | WO 2008/040969 | 4/2008 |

* cited by examiner

*Primary Examiner* — Jafar Parsa
(74) *Attorney, Agent, or Firm* — Steven D. Boyd

(57) ABSTRACT

The subject of the invention is a process for the purification of 2,3,3,3-tetrafluoro-1-propene (HFO-1234yf). More particularly, it relates to a purification process in which 2,3,3,3-tetrafluoro-1-propene, comprising impurities based on halogen compounds, is brought into contact with an adsorbent, preferably molecular sieves and advantageously molecular sieves having a pore opening with an average diameter between 5 and 11 Å, preferably between 5 and 9 Å.

4 Claims, No Drawings

PROCESS FOR THE PURIFICATION OF 2,3,3,3-TETRAFLUORO-1-PROPENE (HFO-1234YF)

FIELD OF THE INVENTION

The invention relates to a process for purifying 2,3,3,3-tetrafluoro-1-propene (HFO 1234yf).

TECHNICAL BACKGROUND

Hydrofluorocarbons (HFCs) and in particular hydrofluoroolefins (HFOs), such as 2,3,3,3-tetrafluoro-1-propene (HFO 1234yf) are compounds that are known for their properties as coolants and heat-exchange fluids, extinguishing agents, propellants, foaming agents, swelling agents, gaseous dielectrics, polymerization medium or monomer, support fluids, agents for abrasives, drying agents and fluids for energy production units. Unlike CFCs and HCFCs, which are potentially hazardous to the ozone layer, HFOs do not contain chlorine and thus pose no problem to the ozone layer.

HFO 1234yf may be obtained by dehydrofluorination of a pentafluoropropane. The reagent concerned may be 1,1,1,2,3-pentafluoropropane (HFC 245eb), as described in document WO 2008/002 500, or 1,1,1,2,2-pentafluoro-propane (HFC 245cb), as described in document WO 2007/079 435. These pentafluoropropanes are prepared by fluorination in the liquid or gaseous phase of chloro or chlorofluoro compounds or via successive dehydrohalogenation and hydrogenation reactions. Document U.S. Pat. No. 5,396,000 describes, for example, the preparation of 1,1,1,2,3-pentafluoropropane (HFC 245eb) via catalytic dehydrohalogenation of 1,1,1,2,3,3-hexa-fluoropropane (HFC 236ea) into 1,2,3,3,3-pentafluoro-1-propene (HFO 1225ye), followed by a hydrogenation to produce the desired compound.

HFO 1234yf may more generally be obtained by dehydrohalogenation of a tetrafluorohalopropane. The reagent concerned may be 1,1,1,2-tetrafluoro-3-iodopropane, as described in document WO 2005/108 334, or 1,1,1,2-tetrafluoro-2-chloropropane (HCFC 244bb), as described in documents WO 2007/079 431 and WO 2008/040 969.

All these processes start from or proceed via saturated halofluoro compounds. On account of the large differences in volatility between these saturated halofluoro compounds and HFO 1234yf, they may generally be separated via standard distillation processes. However, out of concern for obtaining a product of maximum purity, it is appropriate to lower the residual concentration of saturated impurities.

The use of adsorbent solids for the purification of fluoro compounds is already known. The purification treatments are usually performed at room temperature or in the region thereof.

Document JP 2002/226411 describes the purification of 1,1,1,3,3-pentafluoropropane (HFC 245fa) comprising between 5 ppm and 2% by weight of halopropene, such as fluoropropene and chlorofluoropropene, using a solid adsorbent, especially active charcoal.

Document U.S. Pat. No. 7,084,315 describes the removal of olefinic impurities in a hydrofluoroalkane, typically the removal of 1-chloro-2,2-difluoroethylene (F1122) in 1,1,1,2-tetrafluoroethane (F134a) over molecular sieves. HFO 1234yf may be present as impurity.

Document U.S. Pat. No. 7,041,264 describes a process for purifying octafluoropropane, comprising a step of placing crude octafluoropropane containing impurities in contact at high temperature with an impurity-decomposing agent, followed by a step of removing these impurities, for example using an adsorbent. The preferred decomposing agent comprises an iron oxide and an alkaline-earth metal compound.

Document U.S. Pat. No. 7,094,935 describes a method for purifying octafluoropropane or octafluorocyclobutane using an adsorbent obtained according to a process comprising (i) a step of acidic washing of charcoal, followed by washing with water, (ii) a step of deoxidation and/or dehydration of the charcoal, (iii) a recarbonization step at between 500 and 700° C. and an activation step at a temperature of between 700 and 900° C. under a gaseous stream comprising an inert gas, carbon dioxide and water vapor.

Document WO 2007/144 632 describes the use of molecular sieves, with pore sizes of between 3 and 5 Å, for controlling the humidity level of a refrigerant fluid comprising a fluoropropene, especially HFO 1234yf, optionally mixed with iodotrifluoromethane and/or a lubricant.

Document JP 1040507 teaches the use of molecular sieves for reducing the content of perfluoro-2-butyne, an impurity present in hexafluoropropene, to less than 5 ppm.

In patent WO 08/001 844, crude hexafluoropropene is placed in contact with an adsorbent comprising a zeolite whose micropores have a mean diameter of between 3.4 and 11 Å and/or a charcoal-based adsorbent whose micropores have a mean diameter of between 3.5 and 11 Å, for reducing the content of chloro compounds and/or of hydrocarbons in the hexafluoropropene.

DETAILED DESCRIPTION OF THE INVENTION

There is a need for a process for obtaining HFO 1234yf of high purity. One subject of the invention is thus a process for purifying 1234yf starting with a crude HFO 1234yf comprising impurities based on halogenated carbon compounds. The halogenated carbon compounds may be unsaturated or saturated. Saturated halogenated compounds that may especially be mentioned include HFC 245 (pentafluoropropane), HFC 236 (hexafluoropropene), HFC 254 (tetrafluoropropane) and HCFC 244 (monochlorotetrafluoropropene).

It has been found that the impurities based on halogenated compounds present in an HFO 1234yf can be removed (partially or totally) by placing a crude HFO 1234yf in contact with an adsorbent. The purification process according to the present invention is characterized in that the HFO 1234yf, comprising impurities based on halogenated compounds, is placed in contact with an adsorbent, preferably molecular sieves and advantageously molecular sieves with a mean pore diameter of between 5 and 11 Å and preferably between 5 and 9 Å.

Molecular sieves, also known as synthetic zeolites, are chemical compounds widely used in the industry as adsorbents, especially for drying gases or liquids. They are metal aluminosilicates that have a three-dimensional crystal structure formed from an assembly of tetrahedra. These tetrahedra are formed by four oxygen atoms that occupy the apices, and which surround either a silicon atom or an aluminum atom placed at the center. These structures generally contain cations to make the system electrically neutral, such as those derived from sodium, potassium or calcium.

The molecular sieves that are suitable for use are preferably those of the type A and of the type X and advantageously those of the type X.

In the case of molecular sieves "of the type A", the tetrahedra are assembled such that they compose a truncated octahedron. These octahedra are themselves arranged in a simple cubic crystal structure, forming a network whose cavities have an approximate diameter of 11.5 Å. These cavities are accessible via apertures, or pores, that can be partially blocked with cations. When these cations are derived from sodium, these cavities have an aperture diameter of 4.1 Å, which then gives a "4 A" molecular sieve. The crystal structure of such a sieve may be represented by the following chemical formula:

$$Na_{12}[(AlO_2)_{12}(SiO_2)_{12}].XH_2O$$

in which X, which represents the number of water molecules belonging to the structure (water of crystallization), may be up to 27, which represents 28.5% by weight of the anhydrous zeolite.

After removing the water of crystallization by heating at a temperature from about 500 to 700° C., the cavities of these substances are available for the selective adsorption of various gases or liquids. Thus, the pores of the various types of zeolite allow the passage and adsorption in the corresponding cavities only of molecules whose effective diameter is less than or equal to the effective pore diameter. In the case of drying gases or liquids, it is thus water molecules that are retained by selective adsorption in the cavities mentioned previously, the substance to be dried being itself not or only sparingly adsorbed.

The size of the apertures (or pores) may, moreover, be modified according to the different types of molecular sieve. Thus, by exchanging a large proportion of the sodium ions of a 4A molecular sieve with potassium ions, the 3A molecular sieve is obtained, the pores of which have a diameter of about 3 Å. The 5A molecular sieve is prepared by replacing the sodium ions with calcium ions, the effective pore diameter then being about 5 Å.

The elementary cell of zeolite X is a tetrahedron whose apices are occupied by polyhedra of the same type as those present in zeolite A, each being connected to four other polyhedra by virtue of an octahedral substructure, formed by a double ring containing eight oxygen atoms. The center of each edge is always occupied by an oxygen atom, whereas the silicon and aluminum atoms occupy the various apices of the polyhedra. The empirical formula is of the structure $Na_{88}Al_{88}Si_{104}O_{384}.220H_2O$.

The process according to the invention is suitable for the purification of a crude HFO 1234yf with a purity of at least 85% by weight, preferably greater than 90% by weight and advantageously greater than 95% by weight.

The crude HFO 1234yf subjected to the purification step may originate directly from the effluent obtained from the manufacturing step, after optional separation such as decantation or distillation.

The impurities based on saturated halogenated compounds present in the HFO 1234yf are especially 245eb ($CF_3$—CHF—$CH_2F$), 245cb ($CF_3$—$CF_2$—$CH_3$), 236ea ($CF_3$—CHF—$CHF_2$), 1,1,1,2-tetrafluoro-3-chloropropane and tetrafluoropropane. The impurities based on unsaturated halogenated compounds are especially fluoropropenes, such as 1,1,1,2,3-pentafluoropropene, 1,1,1,3,3-pentafluoropropene and 1,1,1-trifluoropropene.

The placing in contact with the adsorbent to purify the crude HFO 1234yf may be performed in the gaseous phase or in the liquid phase at a temperature of between −20° C. and +80° C. and preferably between +10° C. and +40° C., and at a pressure from 100 to 2200 kPa, preferably at atmospheric pressure.

For the gaseous-phase treatment, a flow rate corresponding to a throughput of between 10 and 40 g/h of crude HFO 1234yf may be used for an amount of adsorbent of between 10 and 50 g. The example that follows illustrates the invention without limiting it.

EXAMPLE

Example 1

A charge of 30 g of CECA G5 molecular sieves (sodium silicoaluminate, zeolite of type X) with pore diameters of 7.8 Å and a pore volume of 0.24 cm$^3$/g was placed in a stainless-steel tube 70 cm long and with an inside diameter of 16 mm, comprising a metal grille at the bottom. A gaseous stream of 1234yf containing 0.38% of 236ea, 6.42% of 245eb and 1.17% of 254 passed through the zeolite bed at room temperature and atmospheric pressure and at a throughput of 32 g/h. A total amount of product of 95.6 g was introduced in gaseous form through the bed of molecular sieves over a period of about 3 hours. 88.6 g of product were recovered at the outlet. The yield is thus 92.7%. The composition on entering and exiting is given in Table 1.

The analyses are performed before and after passing over the molecular sieves, using a gas chromatograph equipped with a CarbopackB/1% SP1000 column.

TABLE 1

Analytical results before and after passing over the zeolite bed

| | Mol % | | | | | | | |
|---|---|---|---|---|---|---|---|---|
| | 1234yf | 1225zc | 1225yeZ | F254 | 1225yeE | 1234zeZ | 245eb | 236ea |
| Starting analysis | 87.5 | 0.46 | 3.51 | 1.17 | 0.14 | 0.13 | 6.42 | 0.38 |
| Ex. 1 | 96.2 | 0.42 | 2.97 | <10 ppm | 0.1 | <10 ppm | <10 ppm | <10 ppm |

The invention claimed is:

1. A purification process for purifying 2,3,3,3-tetrafluoropropene comprising contacting 2,3,3,3-tetrafluoropropene having containing saturated halogenated impurities with a molecular sieve having a mean pore diameter of between 5 and 11 Å, whereby said saturated halogenated impurities are separated from said 2,3,3,3-tetrafluoropropene.

2. The purification process as claimed in claim 1, characterized in that the molecular sieve is of the X or A type.

3. The purification process as claimed in claim 1, characterized in that the saturated halogenated impurities are selected from the group consisting of 1,1,1,2,3-pentafluoropropane, 1,1,1,2,2-pentafluoropropane, 1,1,1,2,3,3-hexafluoropropane and mixtures thereof.

4. The purification process as claimed in claim 1, characterized in that the molecular sieve has a mean pore diameter of between 5 and 9 Å.

* * * * *